(12) United States Patent
Shi et al.

(10) Patent No.: US 11,384,162 B2
(45) Date of Patent: Jul. 12, 2022

(54) CATECHOL GROUP MODIFIED BIOMACROMOLECULAR SCAFFOLD MATERIAL AND PREPARATION METHOD THEREOF

(71) Applicant: JIANGNAN UNIVERSITY, Jiangsu (CN)

(72) Inventors: Dongjian Shi, Jiangsu (CN); Jiali Shen, Jiangsu (CN); Zhuying Zhang, Jiangsu (CN); Chuanhao Cao, Jiangsu (CN); Qian Zhao, Jiangsu (CN); Xiaojie Li, Jiangsu (CN); Mingqing Chen, Jiangsu (CN)

(73) Assignee: JIANGNAN UNIVERSITY, Wuxi (CN)

( * ) Notice: Subject to any disclaimer, the term of this patent is extended or adjusted under 35 U.S.C. 154(b) by 362 days.

(21) Appl. No.: 16/071,027

(22) PCT Filed: Aug. 31, 2017

(86) PCT No.: PCT/CN2017/099809
§ 371 (c)(1),
(2) Date: Jul. 18, 2018

(87) PCT Pub. No.: WO2018/045905
PCT Pub. Date: Mar. 15, 2018

(65) Prior Publication Data
US 2019/0062462 A1 Feb. 28, 2019

(30) Foreign Application Priority Data
Sep. 7, 2016 (CN) .......................... 201610806003.3

(51) Int. Cl.
| | | |
|---|---|---|
| C08B 37/00 | (2006.01) |
| A61L 27/58 | (2006.01) |
| A61L 27/50 | (2006.01) |
| C08G 69/10 | (2006.01) |
| A61L 27/26 | (2006.01) |
| A61L 27/18 | (2006.01) |
| A61L 27/20 | (2006.01) |
| A61L 27/56 | (2006.01) |
| C08B 37/08 | (2006.01) |
| C08G 69/02 | (2006.01) |
| C08G 69/48 | (2006.01) |

(52) U.S. Cl.
CPC .......... C08B 37/0084 (2013.01); A61L 27/18 (2013.01); A61L 27/20 (2013.01); A61L 27/26 (2013.01); A61L 27/50 (2013.01); A61L 27/56 (2013.01); A61L 27/58 (2013.01); C08B 37/003 (2013.01); C08B 37/0072 (2013.01); C08G 69/02 (2013.01); C08G 69/10 (2013.01); C08G 69/48 (2013.01); A61L 2400/18 (2013.01); A61L 2430/00 (2013.01); A61L 2430/02 (2013.01)

(58) Field of Classification Search
CPC .......... A61L 27/18; A61L 27/20; A61L 27/26; A61L 27/50; A61L 27/56; A61L 27/58; A61L 2400/18; A61L 2430/00; A61L 2430/02; C08B 37/003; C08B 37/0072; C08B 37/0084; C08G 69/02; C08G 69/10; C08G 69/48
See application file for complete search history.

(56) References Cited

FOREIGN PATENT DOCUMENTS

| CN | 102964610 A | 3/2013 |
|---|---|---|
| CN | 105079884 A | 11/2015 |
| CN | 105801897 A | 7/2016 |
| CN | 106267337 A | * 1/2017 |
| CN | 106267337 A | 1/2017 |
| CN | 106377797 A | 2/2017 |
| KR | 20110134790 A | 12/2011 |
| WO | 2013074748 A | 5/2013 |

OTHER PUBLICATIONS

Yang, et al. "Polydopamine-mediated surface modification of scaffold materials for human neural stem cell engineering", Biomaterials 33 (2012) 6952-6964. (Year: 2012).*
CN106267337 English Machine Translation, prepared Mar. 27, 2020 (Year: 2020).*
Rui Wang etc., "A Biomimetic Mussel-Inspired ε-Poly-Hysine Hydrogel with Robust Tissue-Anchor and Anti-Infection Capacity", Adv. Funct. Mater. 2017, 27, 1604894.
Zhenming Wang etc., "Bioadhesive Microporous Architectures by Self-Assembling Polydopamine Microcapsules for Biomedical Applications", Chem. Mater. 2015, 27, 848-856.
Sara Azevedo etc., "Bioinspired Ultratough Hydrogel with Fast Recovery, Self-Healing, Injectability and Cytocompatibility", Adv. Mater. 2017, 29, 1700759.

(Continued)

*Primary Examiner* — Christopher M Rodd
(74) *Attorney, Agent, or Firm* — Enshan Hong; VLP Law Group LLP (57) ABSTRACT

The invention discloses a preparation method of a catechol group modified biomacromolecular scaffold material, comprising: grafting a catechol-containing compound by amidation to obtain modified biomacromolecules; then, allowing dopamine to perform oxidized self-polymerization in a weakly alkaline buffer solution to form polydopamine (PDA) particles with a uniform particle size; next, forming a scaffold which has three cross-linking structures, namely modified biomacromolecules, modified biomacromolecules/PDA, and biomacromolecules/PDA, through interaction between catechol groups, interaction between catechol groups and PDA particles, and interaction between macromolecules and PDA particles in the modified macromolecules respectively; and cross-linking the scaffold with calcium ions, adipic dihydrazide or genipin to further adjust the degree of cross-linking and porosity of the scaffold. The prepared scaffold material has excellent biocompatibility and biodegradability, can promote cell adhesion, and has a wide application prospect in the field of tissue repair and regeneration.

17 Claims, 2 Drawing Sheets

(56) References Cited

OTHER PUBLICATIONS

Kyuri Kim etc., "Chitosan-catechol: A polymer with long-lasting mucoadhesive properties", Biomaterials 52 (2015) 161e170.
Jinke Xu etc., "Genipin-crosslinked catechol-chitosan mucoadhesive hydrogels for buccal drug delivery", Biomaterials 37 (2015) 395-404.
Jisoo Shin etc., "Mussel Adhesion-Inspired Reverse Transfection Platform Enhances Osteogenic Differentiation and Bone Formation of Human Adipose-Derived Stem Cells", small 2016, 12, No. 45, 6266-6278.
Jisoo Shin etc., "Tissue Adhesive Catechol-Modified Hyaluronic Acid Hydrogel for Effective, Minimally Invasive Cell Therapy", Adv. Funct. Mater. 2015, DOI: 10.1002/adfm.201500006.
Lu Han et al., "Tough, self-healable and tissue-adhesive hydrogel with tunable multifunctionality", NPG Asia Materials (2017) 9, e372; doi:10.1038/am.2017.33.

\* cited by examiner

CATECHOL GROUP MODIFIED BIOMACROMOLECULAR SCAFFOLD MATERIAL AND PREPARATION METHOD THEREOF

RELATED APPLICATIONS

This is a U.S. national stage of international application No. PCT/CN2017/099809 filed on Aug. 31, 2017, which claims priority from China Patent Application No. 201610806003.3 filed on Sep. 7, 2016, the entire content of which is incorporated herein as reference.

BACKGROUND OF THE INVENTION

Technical Field

The invention relates to the technical field of macromolecular materials and biological materials, specifically to a catechol group modified biomacromolecular scaffold material and a preparation method thereof.

Description of Related Art

Bone tissues have good regeneration and self-repair capabilities, and small tissue defects can be completely self-healed. However, when a tissue defect exceeds a critical limit, self-repair does not work, and surgery is needed to perform implantation for treatment. At present, two relatively effective methods are employed to repair defects in bone tissues, namely autogenous bone graft and allogenic bone transplantation. The autogenous bone graft is regarded as the "gold standard" of bone transplantation, but also has some shortcomings, for example, limited sources of materials, tendency to cause infections to tissues, tendency to cause secondary injuries to patients, etc. The allogenic bone transplantation is limited in use in the bone defect repair field because of high surgery cost, tendency to cause immunological rejection and tendency to cause viral infections. In order to overcome the limits of autogenous bone graft and allogenic bone transplantation, researchers have been striving to research and develop ideal artificial bone repair materials for repairing and re-building bone tissues.

At present, artificial bone repair scaffolds for repairing bone tissues are mainly classified into three types: metal, ceramic and polymeric scaffolds. Among the three types, metal and ceramic brackets are relatively high in hardness, but poor biocompatibility and relatively weak in bonding with surrounding tissue interfaces. Additional defects are poor biodegradability, high fragility, and so on. The macromolecular materials include two types, namely biomacromolecular materials and synthesized macromolecular materials, which have relatively high structure adjustability, biocompatibility and biodegradability. These macromolecular materials have been applied to the construction of scaffold materials. As the research and development of scaffold materials continuously go further, researchers found that the interactions between cells and materials and the performance of material surfaces have a great significance for the repair of bone defects. Macromolecular scaffold materials have many advantages in applications, but still have defects. It is a great challenge to construct a scaffold material which has strong interaction with tissue interfaces and has active control-released biological factors and of which the structure, physical strength, and degradation cycle are matched with those of the surrounding tissues.

Inspired by marine mussels which can temporarily or permanently stick to various material surfaces, a huge amount of 3,4-dihydroxyphenylalanine (DOPA) that provides high adhesion was found to be existed in filopodium proteins of mussels after researches on marine mussels. In the DOPA, groups that provide adhesion are mainly catechol groups. Dopamine (DA) and 3,4-dihydroxyphenylpropionic acid (HCA), the derivatives of DOPA, are two common compounds containing catechol groups. The DA can perform oxidized self-polymerization in a wet state, and its self-polymerized product, namely polydopamine (PDA), has super-high adhesion to various material surfaces and even super-hydrophobic surfaces, and is adjustable in thickness of an adhesive layer and high in stability. With certain induction conditions, the DA and self-polymerization products of its derivatives can be further combined to form polydopamine (PDA) nano-particles in solutions. The formed polydopamine or polydopamine nano-particles contain a lot of catechol or diquinone structures which can perform Michael addition and Schiff base reactions with compounds that contain hydrosulphonyl, amino, and imino groups in mild conditions. Therefore, modification with the DA provides an approach for secondary modification of materials. Besides, PDA is also a kind of natural melanin. The melanin is a biological pigment which endows PDA with excellent biocompatibility, generates relatively small injuries to human cells, and does not cause human immune responses. On the basis of super-high adhesion and excellent biocompatibility, PDA is expected to improve adhesion to material surfaces and promote cell adhesion to manufacture ideal tissue repair materials.

BRIEF SUMMARY OF THE INVENTION

For this reason, the objective of the invention is to provide a preparation method of a catechol group modified biomacromolecular scaffold material to obtain materials which have excellent biocompatibility, biodegradability, and cell adhesion and can effectively promote tissue repair and regeneration.

The design concept of the invention is as follows. By using the reactivity of many catechol groups, the catechol groups and biomolecules perform amidation to obtain a biologically modified macromolecule; then, a sacffold with three types of cross-linking structures is prepared by using the oxidized polymerization and adhesion of the DA; next, calcium ions or adipic dihydrazide, and genipin are used to perform further cross-linking to adjust the degree of cross-linking and porosity of the scaffold, thus obtaining a dopamine-based scaffold material.

The technical scheme of the invention is as follows. Through amidation, catechol group modified biomacromolecules with chemical reactivity, oxidized polymerization and excellent adhesion are used to synthesize biologically modified macromolecules; a three-dimensional-networked scaffold is obtained by making use of the interaction between catechol groups, the interaction between catechol groups and polydopamine particles, and the interaction between the biological macromolecules and polydopamine particles in the modified macromolecules; next, calcium ions or adipic dihydrazide or genipin is further used to cross-link the scaffold to adjust the degree of cross-linking and porosity of the scaffold; after cross-linking, the obtained product is washed with super-pure water and then is freeze-dried for 48 h to obtain a scaffold material which has three types of cross-linking structures, namely modified biomacromolecules, modified biomacromolecules/polydopamine, and biomacromolecules/polydopamine.

In the invention, the feeding ratio of biomacromolecules to a catechol radical-containing compound is 2:1-1:5 during amidation, and the substitution degree of the catechol radicals in the modified biomacromolecules is 16-60%; the concentrations of the biomacromolecules and the modified biomacromolecules both are 4% in super-pure water; the concentration of polydopamine particles is 0.1%, while the particle size of the polydopamine particles is controlled to be within a range of 150-560 nm; and the concentration of the calcium ions is 5%.

The preparation method provided by the invention takes catechol radicals as functional radicals and employs physically or chemically modified biomacromolecules to prepare catechol radical modified biomacromolecules. A scaffold which has three cross-linking structures, namely modified biomacromolecules, modified biomacromolecules/polydopamine, and biomacromolecules/polydopamine, is formed through interaction between catechol radicals, interaction between catechol radicals and polydopamine particles, and interaction between macromolecules and polydopamine particles in the modified macromolecules, respectively. Then, calcium ions or adipic dihydrazide or genipin is/are employed to cross-link the scaffold to further adjust the degree of cross-linking and porosity of the scaffold. In this way, the obtained catechol group modified biomacromolecular scaffold material has excellent biocompatibility, biodegradability and cell adhesion, can effectively promote tissue repair and regeneration, and has a wide application prospect in the field of tissue repair and regeneration.

The invention has the beneficial advantage of simply and quickly preparing the catechol group modified biomacromolecular scaffold material with a freeze-drying method. Macromolecules are selected as bone materials of the scaffold, endowing the scaffold with excellent biocompatibility and biodegradability. By using the adhesion of the dopamine, the scaffold can effectively stick to cells, and the scaffold is driven to quickly bond with tissue interfaces, thus effectively promoting regeneration of tissues, and achieving a potential application value of tissue repair.

The porosity of the catechol group modified biomacromolecular scaffold material can be controlled to be within the range of 88-91%. The catechol group modified biomacromolecular scaffold material (three-dimensional scaffold material) is not toxic to living bodies and can degrade in a PBS buffer solution. The catechol group modified biomacromolecular scaffold material can degrade about 15-50% within 30 days, and completely degrade within 90 days.

DETAILED DESCRIPTION OF THE INVENTION

To clarify the objective, technical scheme, and advantages of the invention, the invention is described in further detail in conjunction with the following attached drawings and embodiments.

Embodiment 1 Synthesis of Alginic Acid-Dopamine (Alg-DA) Modified Macromolecules 1 g of alginic acid (Alg) was weighed and placed in a three-mouth flask; then 100 mL of PBS buffer solution (50 mM, pH=5.5) was added into the flask; Alg was stirred at room temperature to be dissolved; after Alg was completely dissolved, 1.94 g of 1-ethyl-3-(3-dimethylaminopropyl) carbodiimide (EDC) and 2.32 g of N-hydroxy succinimide (NETS) were added into the flask in turn, wherein n(COOH)/n(EDC)/n(NHS)=1/2/4; the mixture was activated for 30 min at room temperature; and then, 0.479 g of dopamine hydrochloride (DA) was added, wherein n(Alg)/n(DA)=2:1. The flask was repeatedly vacuumed and then supplied with nitrogen gas for three cycles to eliminate air in the three-mouth flask and prevent the DA from being oxidized.

In the nitrogen atmosphere, the reaction proceeded for 24 h at room temperature. After the reaction stopped, reaction products were dialyzed with deionized water to remove EDC, NETS and unreacted monomers in the reaction products until no dopamine ultraviolet absorption peak was found in the dialysate. Then, the dialysis product was freeze-dried to obtain white cotton-like biologically modified macromolecules Alg-DA.

Embodiment 2 Synthesis of Alginic Acid-Dopamine (Alg-DA) Modified Macromolecules 1 g of alginic acid (Alg) was weighed and placed in a three-mouth flask; then 100 mL of PBS buffer solution (50 mM, pH=5.5) was added into the flask; Alg was stirred at room temperature to be dissolved; after the Alg was completely dissolved, 1.94 g of 1-ethyl-(3dimethylaminopropyl) carbodiimide (EDC) and 2.32 g of N-hydroxy succinimide (NETS) were added into the flask in turn, wherein n(COOH)/n(EDC)/n(NHS)=1/2/4; the mixture was activated for 30 min at room temperature; and then, 0.958 g of dopamine hydrochloride (DA) was added, wherein n(Alg)/n(DA)=1:1. The flask was repeatedly vacuumed and then supplied with nitrogen gas for three cycles to eliminate air in the three-mouth flask and prevent the DA from being oxidized.

Figure 1:
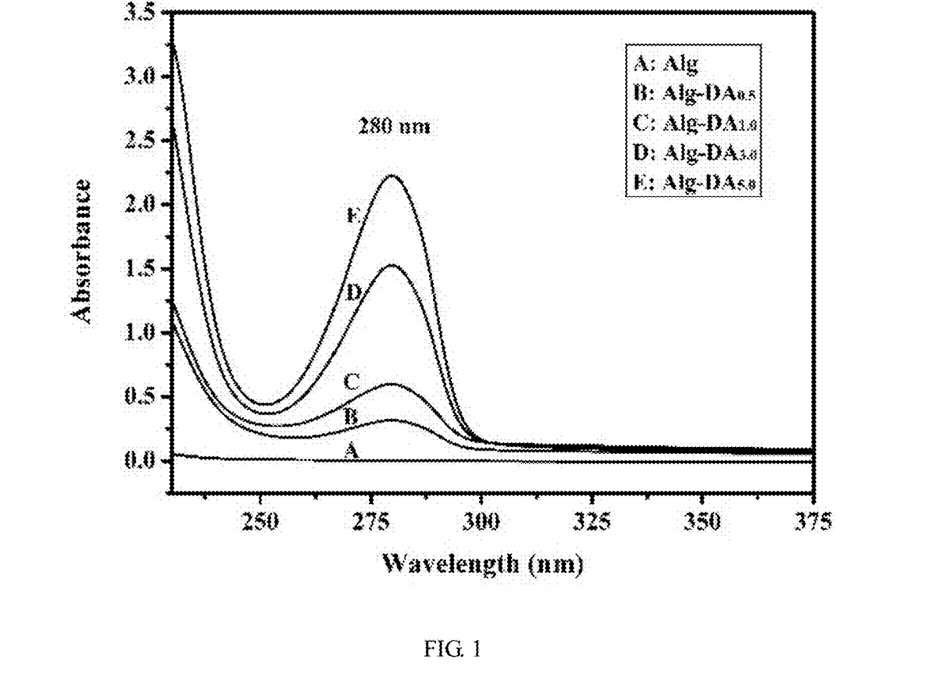
FIG. 1 is a UV-visible light spectrogram of alginic acid-dopamine in an embodiment of the invention.
Figure 2:
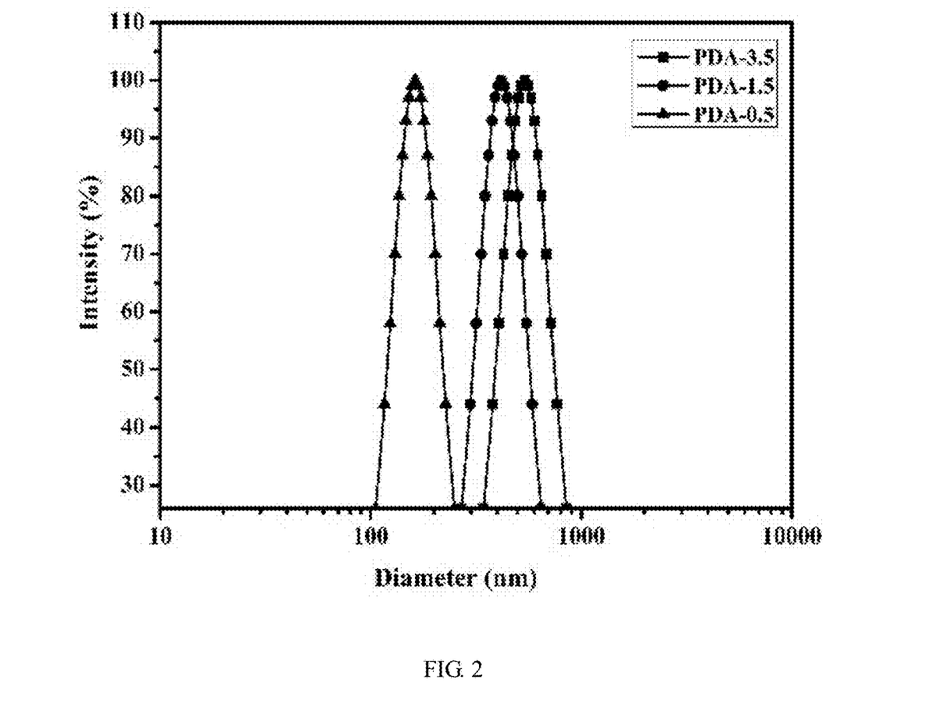
FIG. 2 is a particle size distribution diagram of polydopamine in an embodiment of the invention.
Figure 3:
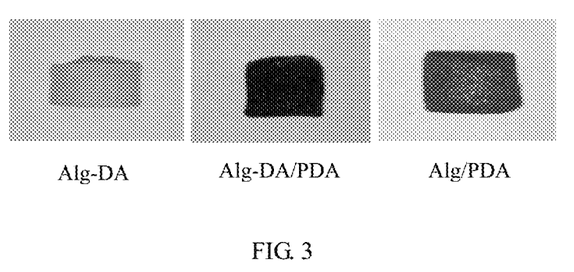
FIG. 3 is a picture of a dopamine-based scaffold material in an embodiment of the invention.

In the nitrogen gas atmosphere, a reaction proceeded for 20 h at room temperature. After the reaction stopped, reaction products were dialyzed with deionized water to remove EDC, NHS and unreacted monomers in the reaction products until no dopamine ultraviolet absorption peak was found in the dialysate. Then, the dialysis product was freeze-dried to obtain white cotton-like biologically modified macromolecules Alg-DA. The UV-visible light spectrogram of the Alg-DA can be seen in FIG. 1.

Embodiment 3 Synthesis of Alginic Acid-Dopamine (Alg-DA) Modified Macromolecules 1 g of alginic acid (Alg) was weighed and placed in a three-mouth flask; then 100 mL of PBS buffer solution (50 mM, pH=5.5) was added into the flask; Alg was stirred at room temperature to be dissolved; after Alg was completely dissolved, 1.94 g of 1-ethyl-(3-dimethylaminopropyl) carbodiimide (EDC) and 2.32 g of N-hydroxy succinimide (NETS) were added into the flask in turn, wherein n(COOH)/n(EDC)/n(NHS)=1/2/4; the mixture was activated for 30 min at room temperature; and then, 2.87 g of dopamine hydrochloride (DA) was added, wherein n(Alg)/n(DA)=1:3. The flask was repeatedly vacuumed and then supplied with nitrogen gas for three cycles to eliminate air in the three-mouth flask and prevent the DA from being oxidized.

In the nitrogen gas atmosphere, a reaction proceeded for 26 h at room temperature. After the reaction stopped, reaction products were dialyzed with deionized water to remove EDC, NETS and unreacted monomers in the reaction products until no dopamine ultraviolet absorption peak was found in the dialysate. Then, the dialysis product was freeze-dried to obtain white cotton-like biologically modified macromolecules Alg-DA.

Embodiment 4 Synthesis of Alginic Acid-Dopamine (Alg-DA) Modified Macromolecules 1 g of alginic acid (Alg) was weighed and placed in a three-mouth flask; then 100 mL of PBS buffer solution (50 mM, pH=5.5) was added into the flask; Alg was stirred at room temperature to be dissolved; after Alg was completely dissolved, 1.94 g of 1-ethyl-(3-dimethylaminopropyl) carbodiimide (EDC) and 2.32 g of N-hydroxy succinimide (NETS) were added into the flask in turn, wherein n(COOH)/n(EDC)/n(NHS)=1/2/4; the mixture was activated for 30 min at room temperature; and then, 4.79 g of dopamine hydrochloride (DA) was added, wherein n(Alg)/n(DA)=1:5. The flask was repeatedly vacuumed and then supplied with nitrogen gas for three cycles to eliminate air in the three-mouth flask and prevent the DA from being oxidized.

In the nitrogen gas atmosphere, a reaction proceeded for 19 h at room temperature. After the reaction stopped, reaction products were dialyzed with deionized water to remove EDC, NETS and unreacted monomers in the reaction products until no dopamine ultraviolet absorption peak was found in the dialysate. Then, the dialysis product was freeze-dried to obtain white cotton-like biologically modified macromolecules Alg-DA.

Embodiment 5 Synthesis of Hyaluronic Acid-Dopamine (HA-DA) Modified Macromolecules 1 g of hyaluronic acid (AH) was weighed and placed in a three-mouth flask; then 100 mL of PBS buffer solution (50 mM, pH=5.5) was added into the flask; Alg was stirred at room temperature to be dissolved; after Alg was completely dissolved, 1.01 g of 1-ethyl-(3-dimethylaminopropyl) carbodiimide (EDC) and 1.21 g of N-hydroxy succinimide (NHS) were added into the flask in turn, wherein n(COOH)/n(EDC)/n(NHS)=1/2/4; the mixture was activated for 30 min at room temperature; and then, 0.250 g of dopamine hydrochloride (DA) was added, wherein n(Alg)/n(DA)=2:1. The flask was repeatedly vacuumed and then supplied with nitrogen gas for three cycles to eliminate air in the three-mouth flask and prevent the DA from being oxidized.

In the nitrogen gas atmosphere, a reaction proceeded for 24 h at room temperature. After the reaction stopped, reaction products were dialyzed with deionized water to remove EDC, NHS and unreacted monomers in the reaction products until no dopamine ultraviolet absorption peak was found in the dialysate. Then, the dialysis product was freeze-dried to obtain white cotton-like biologically modified macromolecules HA-DA.

What should be explained is that, when the added amount of the dopamine hydrochloride (DA) in Embodiment 5 was changed into 0.50 g, 1.50 g, and 2.50 g (namely n(HA)/n(DA) was 1:1, 1:3, and 1:5 respectively), HA-DA with different degrees of substitution can be obtained.

Embodiment 6 Synthesis of Polyglutamic Acid-Dopamine (γ-PGA-DA) Modified Macromolecules 1 g of polyglutamic acid-dopamine (γ-PGA) was weighed and placed in a three-mouth flask; then 100 mL of PBS buffer solution (50 mM, pH=5.5) was added into the flask; Alg was stirred at room temperature to be dissolved; after Alg was completely dissolved, 2.97 g of 1-ethyl-(3-dimethylaminopropyl) carbodiimide (EDC) and 3.57 g of N-hydroxy succinimide (NETS) were added into the flask in turn, wherein n(COOH)/n(EDC)/n(NHS)=1/2/4; the mixture was activated for 30 min at room temperature; and then, 0.735 g of dopamine hydrochloride (DA) was added, wherein n(γ-PGA)/n(DA)=2:1. The flask was repeatedly vacuumed and then supplied with nitrogen gas for three cycles to eliminate air in the three-mouth flask and prevent the DA from being oxidized.

In the nitrogen gas atmosphere, a reaction proceeded for 22 h at room temperature. After the reaction stopped, reaction products were dialyzed with deionized water to remove EDC, NHS and unreacted monomers in the reaction products until no dopamine ultraviolet absorption peak was found in the dialysate. Then, the dialysis product was freeze-dried to obtain white cotton-like biologically modified macromolecules γ-PGA-DA.

What should be explained is that, when the added amount of the dopamine hydrochloride (DA) in Embodiment 6 was changed into 1.47 g, 4.41 g, and 7.35 g (namely n(γ-PGA)/n(DA) was 1:1, 1:3, and 1:6 respectively), γ-PGA-DA of different degrees of substitution can be obtained.

Embodiment 7 Synthesis of chitosan-3,4-dihydroxyphenylpropionic acid (CS-HCA) Modified Macromolecules 1 g of chitosan (CS) was weighed and placed into a three-mouth flask; then, 80 mL of 1 wt % acetum was added into the flask; the materials were stirred at room temperature to be dissolved; 0.563 g of 3,4-dihydroxyphenylpropionic acid (HCA) was dissolved in 10 mL of super-pure water, and then the mixed solution was added into the chitosan-acetum solution; 1-ethyl-(3-dimethylaminopropyl) carbodiimide (EDC) was dissolved in 10 mL of super-pure water, and the obtained solution was dropped into the reaction system, wherein n(CS)/n(HCA)=1:2. The flask was repeatedly vacuumed and then supplied with nitrogen gas for three cycles to eliminate air in the three-mouth flask and prevent HCA from being oxidized.

In the nitrogen gas atmosphere, a reaction proceeded for 24 h at room temperature. After the reaction stopped, reaction products were dialyzed with deionized water to remove EDC and unreacted monomers in the reaction products until no dopamine ultraviolet absorption peak was found in the dialysate. Then, the dialysis product was freeze-dried to obtain yellow-brown cotton-like biologically modified macromolecules CS-HCA.

What should be explained is that, when the added amount of the 3,4-dihydroxyphenylpropionic acid (HCA) in Embodiment 7 was changed into 1.13 g, 3.38 g, and 5.63 g (namely n(CS)/n(HCA) was 1:1, 1:3, and 1:5 respectively), CS-HCA with different degrees of substitution can be obtained.

Embodiment 8 Synthesis of polylysine-3,4-dihydroxyphenylpropionic acid (PL-HCA) Modified Macromolecules 1 g of polylysine (PL) was weighed and placed into a three-mouth flask; then, 80 mL of PBS buffer solution (50 mM, pH=5.5) was added into the flask; the materials were stirred at room temperature to be dissolved; 0.708 g of 3,4-dihydroxyphenylpropionic acid (HCA) was dissolved in 10 mL of PBS buffer solution, and then the mixed solution was added into the buffer solution of polylysine; 1-ethyl-(3-dimethylaminopropyl) carbodiimide (EDC) was dissolved in 10 mL of PBS buffer solution, and then the obtained solution was dropped into the reaction system, wherein n(PL)/n(HCA)=2:1. The flask was repeatedly vacuumed and then supplied with nitrogen gas for three cycles to eliminate air in the three-mouth flask and prevent HCA from being oxidized.

In the nitrogen gas atmosphere, a reaction proceeded for 25 h at room temperature. After the reaction stopped, reaction products were dialyzed with deionized water to remove EDC and unreacted monomers in the reaction products until no dopamine ultraviolet absorption peak was found in the dialysate. Then, the dialysis product was freeze-dried to obtain yellow-brown cotton-like biologically modified macromolecules PL-HCA.

What should be explained is that, when the added amount of the 3,4-dihydroxyphenylpropionic acid (HCA) in Embodiment 7 was changed into 1.42 g, 4.25 g, and 7.08 g (namely n(PL)/n(HCA) was 1:1, 1:3, and 1:5 respectively), PL-HCA with different degrees of substitution can be obtained.

Embodiment 9 Preparation of Polydopamine (PDA) Particles 0.5 g of ammonia water was added into a mixture of ethanol (40 mL) and super-pure water (90 mL), and the mixed materials were stirred for 30 min at a temperature of 30° C. to obtain a mixed solution. Then, 0.5 g of dopamine was dissolved in 10 mL of super-pure water, and the obtained solution was added into the mixed solution; a reaction proceeded for 24 h at a temperature of 30° C.; and reaction products were dialyzed and freeze-dried to obtain PDA particles with a particle size of 560 nm.

Embodiment 10 Preparation of Polydopamine (PDA) Particles 1.5 g of ammonia water was added into a mixture of ethanol (40 mL) and super-pure water (90 mL), and the mixed materials were stirred for 30 min at a temperature of 30° C. to obtain a mixed solution. Then, 0.5 g of dopamine was dissolved in 10 mL of super-pure water, and the obtained solution was added into the mixed solution; a reaction proceeded for 22 h at a temperature of 32° C.; and reaction products were dialyzed and freeze-dried to obtain PDA particles with a particle size of 250 nm.

Embodiment 11 Preparation of Polydopamine (PDA) Particles 3.5 g of ammonia water was added into a mixture of ethanol (40 mL) and super-pure water (90 mL), and the mixed materials were stirred for 30 min at a temperature of 30° C. to obtain a mixed solution. Then, 0.5 g of dopamine was dissolved in 10 mL of super-pure water, and the obtained solution was added into the mixed solution; a reaction proceeded for 25 h at a temperature of 29° C.; and reaction products were dialyzed and freeze-dried to obtain PDA particles with a particle size of 150 nm.

Embodiment 12 Preparation of a Catechol Group Modified Alginic Acid Scaffold Material Alg-DA was dissolved in super-pure water to prepare an Alg-DA solution with a concentration of 4 wt %. The solution was stirred for 8 h, and then was uniformly poured into a die and quickly frozen with liquid nitrogen. After freezing, the material was taken out, placed in a freeze-dryer and freeze-dried for 48 h.

The freeze-dried scaffold material was added into 5 mL of calcium chloride aqueous solution with a mass fraction of 5 wt % to allow cross-linking to proceed. After cross-linking, the scaffold material was washed with super-pure water to remove residual calcium chloride, and freeze-dried for 48 h again, and then the catechol group modified alginic acid scaffold material was obtained. The porosity of the scaffold material was within the range of 88-91%.

Embodiment 13 Preparation of a Catechol Group Modified Hyaluronic Acid Scaffold Material HA-DA was dissolved in super-pure water to prepare an HA-DA solution with a concentration of 2 wt %. The solution was mechanically stirred for 9 h, and then was uniformly poured into a die and quickly frozen with liquid nitrogen. After freezing, the material was taken out, placed in a freeze-dryer and freeze-dried for 50 h.

The freeze-dried scaffold material was cross-linked with 10 mg of adipic dihydrazide. After cross-linking, the scaffold material was washed with super-pure water to remove residual adipic dihydrazide, and freeze-dried for 46 h again, and then the catechol group modified hyaluronic acid scaffold material was obtained. The porosity of the scaffold material was within the range of 88-91%.

Embodiment 14 Preparation of a Catechol Group Modified Polyglutamic Acid Scaffold Material γ-PGA-DA was dissolved in super-pure water to prepare a γ-PGA-DA solution with a concentration of 3 wt %. The solution was mechanically stirred for 6.5 h, and then the solution was uniformly poured into a die and quickly frozen with liquid nitrogen. After freezing, the material was taken out, placed in a freeze-dryer and freeze-dried for 52 h.

The freeze-dried scaffold material was cross-linked with 10 mg of adipic dihydrazide. After cross-linking, the scaffold material was washed with super-pure water to remove residual adipic dihydrazide, and freeze-dried for 48 h again, and then the catechol group modified polyglutamic acid scaffold material was obtained. The porosity of the scaffold material was within the range of 88-91%.

Embodiment 15 Preparation of a Catechol Group Modified Chitosan Scaffold Material CS-HCA was dissolved in super-pure water to prepare a CS-HCA solution with a concentration of 3.5 wt %. The solution was mechanically stirred for 8.2 h, and then was uniformly poured into a die and quickly frozen with liquid nitrogen. After freezing, the material was taken out, placed in a freeze-dryer and freeze-dried for 47.5 h.

The freeze-dried scaffold material was cross-linked with 10 mg of genipin. After cross-linking, the scaffold material was washed with super-pure water to remove residual genipin, and freeze-dried for 50.5 h again, and then the catechol group modified chitosan scaffold material was obtained. The porosity of the scaffold material was within the range of 88-91%.

Embodiment 16 Preparation of a Catechol Group Modified Polylysine Scaffold Material PL-HCA was dissolved in super-pure water to prepare a PL-HCA solution with a concentration of 4.8 wt %. The solution was mechanically stirred for 7 h, and then was uniformly poured into a die and quickly frozen with liquid nitrogen. After freezing, the material was taken out, placed in a freeze-dryer and freeze-dried for 47 h.

The freeze-dried scaffold material was cross-linked with 10 mg of genipin. After cross-linking, the scaffold material was washed with super-pure water to remove residual genipin, and freeze-dried for 44 h again, and then the catechol group modified polylysine scaffold material was obtained. The porosity of the scaffold material was within the range of 88-91%.

Embodiment 17 Preparation of a Catechol Group Modified Alginic Acid/Polydopamine Compound Scaffold Material Alg-DA was dissolved in super-pure water to prepare an Alg-DA solution with a concentration of 4 wt %, and PDA particles were added to obtain an Alg-DA solution, wherein the mass fraction of the PDA particles in the Alg-DA solution was 0.1 wt %. The solution was mechanically stirred for 9 h, and then was uniformly poured into a die and quickly frozen with liquid nitrogen. After freezing, the material was taken out, placed in a freeze-dryer and freeze-dried for 41 h.

The freeze-dried scaffold material was added and cross-linked with 5.5 mL of calcium chloride aqueous solution with a mass fraction of 4.5 wt %. After cross-linking, the scaffold material was washed with super-pure water to remove the residual calcium chloride, and freeze-dried for 53.5 h again, and then the catechol group modified alginic acid/polydopamine compound scaffold material was obtained. The porosity of the compound scaffold material was within the range of 88-91%.

Embodiment 18 Preparation of a Catechol Group Modified Hyaluronic Acid/Polydopamine Compound Scaffold Material HA-DA was dissolved in super-pure water to prepare an HA-DA solution with a concentration of 2.2 wt %, and then 0.1 wt % PDA particles were added into the HA-DA solution. The solution was mechanically stirred for 5 h, and then was uniformly poured into a die and quickly frozen with liquid nitrogen. After freezing, the material was taken out, placed in a freeze-dryer and freeze-dried for 54 h.

The freeze-dried scaffold material was cross-linked with 10 mg of adipic dihydrazide. After cross-linking, the scaffold material was washed with super-pure water to remove residual adipic dihydrazide, and freeze-dried for 48 h again, and then the catechol group modified hyaluronic acid/polydopamine compound scaffold material was obtained. The porosity of the compound scaffold material was within the range of 88-91%.

Embodiment 19 Preparation of a Catechol Group Modified Polyglutamic Acid/Polydopamine Compound Scaffold Material γ-PGA-DA was dissolved in super-pure water to prepare a γ-PGA-DA solution with a concentration of 3 wt %, and then 0.1 wt % PDA particles were added into the γ-PGA-DA solution. The solution was mechanically stirred for 9.2 h, and then was uniformly poured into a die and quickly frozen with liquid nitrogen. After freezing, the material was taken out, placed in a freeze-dryer and freeze-dried for 42.8 h.

The freeze-dried scaffold material was cross-linked with 10 mg of adipic dihydrazide. After cross-linking, the scaffold material was washed with super-pure water to remove residual adipic dihydrazide, and freeze-dried for 51 h again, and then the catechol group modified polyglutamic acid/polydopamine compound scaffold material was obtained. The porosity of the compound scaffold material was within the range of 88-91%.

Embodiment 20 Preparation of a Catechol Group Modified Chitosan/Polydopamine Compound Scaffold Material CS-HCA was dissolved in super-pure water to prepare a CS-HCA solution with a concentration of 3.5 wt %, and then 0.1 wt % PDA particles were added into the CS-HCA solution. The solution was mechanically stirred for 10 h, and then was uniformly poured into a die and quickly frozen with liquid nitrogen. After freezing, the material was taken out, placed in a freeze-dryer and freeze-dried for 48 h.

The freeze-dried scaffold material was cross-linked with 10 mg of genipin. After cross-linking, the scaffold material was washed with super-pure water to remove the residual genipin, and freeze-dried for 40 h again, and then the catechol group modified chitosan/polydopamine compound scaffold material was obtained. The porosity of the compound scaffold material was within the range of 88-91%.

Embodiment 21 Preparation of a Catechol Group Modified Polylysine/Polydopamine Compound Scaffold Material PL-HCA was dissolved in super-pure water to prepare a PL-HCA solution with a concentration of 4.8 wt %, and then 0.1 wt % PDA particles were added into the PL-HCA solution. The solution was mechanically stirred for 10 h, and then was uniformly poured into a die and quickly frozen with liquid nitrogen. After freezing, the material was taken out, placed in a freeze-dryer and freeze-dried for 41.5 h.

The freeze-dried scaffold material was cross-linked with 10 mg of genipin. After cross-linking, the scaffold material was washed with super-pure water to remove residual genipin, and freeze-dried for 52.4 h again, and then the catechol group modified polylysine/polydopamine compound scaffold material was obtained. The porosity of the compound scaffold material was within the range of 88-91%.

Embodiment 22 Preparation of an Alginic Acid/Polydopamine Compound Scaffold Material Alg was dissolved in super-pure water to prepare an Alg solution with a concentration of 4 wt %, and then 0.1 wt % PDA particles were added into the Alg solution. The solution was mechanically stirred for 8.6 h, and then was uniformly poured into a die and quickly frozen with liquid nitrogen.

After freezing, the material was taken out, placed in a freeze-dryer and freeze-dried for 48 h.

The freeze-dried scaffold material was added and cross-linked with 5 mL of calcium chloride aqueous solution with a mass fraction of 5 wt %. After cross-linking, the scaffold material was washed with super-pure water to remove residual calcium chloride, and freeze-dried for 43 h again, and then the alginic acid/polydopamine compound scaffold material was obtained. The porosity of the compound scaffold material was within the range of 88-91%.

Embodiment 23 Preparation of a Hyaluronic Acid/Polydopamine Compound Scaffold Material HA was dissolved in super-pure water to prepare an HA solution with a concentration of 2 wt %, and then 0.1 wt % PDA particles were added into the HA solution. The solution was mechanically stirred for 9.5 h, and then was uniformly poured into a die and quickly frozen with liquid nitrogen. After freezing, the material was taken out, placed in a freeze-dryer and freeze-dried for 38 h.

The freeze-dried scaffold material was cross-linked with 10 mg of adipic dihydrazide. After cross-linking, the scaffold material was washed with super-pure water to remove residual adipic dihydrazide, and freeze-dried for 54 h again, and then the hyaluronic acid/polydopamine compound scaffold material was obtained. The porosity of the compound scaffold material was within the range of 88-91%.

Embodiment 24 Preparation of a Polyglutamic Acid/Polydopamine Compound Scaffold Material γ-PGA was dissolved in super-pure water to prepare a γ-PGA solution with a concentration of 3 wt %, and then 0.1 wt % PDA particles were added into the γ-PGA solution. The solution was mechanically stirred for 8 h, and then was uniformly poured into a die and quickly frozen with liquid nitrogen. After freezing, the material was taken out, placed in a freeze-dryer and freeze-dried for 48 h.

The freeze-dried scaffold material was cross-linked with 10 mg of adipic dihydrazide. After cross-linking, the scaffold material was washed with super-pure water to remove residual adipic dihydrazide, and freeze-dried for 48 h again, and then the polyglutamic acid/polydopamine compound scaffold material was obtained. The porosity of the compound scaffold material was within the range of 88-91%.

Embodiment 25 Preparation of a Chitosan/Polydopamine Compound Scaffold Material CS was dissolved in super-pure water to prepare a CS solution with a concentration of 3.5 wt %, and then 0.1 wt % PDA particles were added into the CS-HCA solution. The solution was mechanically stirred for 11 h, and then was uniformly poured into a die and quickly frozen with liquid nitrogen. After freezing, the material was taken out, placed in a freeze-dryer and freeze-dried for 41 h.

The freeze-dried scaffold material was cross-linked with 10 mg of genipin. After cross-linking, the scaffold material was washed with super-pure water to remove residual genipin, and freeze-dried for 49 h again, and then the chitosan/polydopamine compound scaffold material was obtained. The porosity of the compound scaffold material was within the range of 88-91%.

Embodiment 26 Preparation of a Polylysine/Polydopamine Compound Scaffold Material PL was dissolved in super-pure water to prepare a PL solution with a concentration of 4.8 wt %, and then 0.1 wt % PDA particles were added into the PL solution. The solution was mechanically stirred for 8.8 h, and then was uniformly poured into a die and quickly frozen with liquid nitrogen. After freezing, the material was taken out, placed in a freeze-dryer and freeze-dried for 46 h.

The freeze-dried scaffold material was cross-linked with 10 mg of genipin. After cross-linking, the scaffold material was washed with super-pure water to remove residual genipin, and freeze-dried for 48 h again, and then the polylysine/polydopamine compound scaffold material was obtained. The porosity of the compound scaffold material was within the range of 88-91%.

What should be noted is that, in the invention, room temperature may refer to a temperature within the range of 20-25° C., or 20-30° C., or 15-25° C.

In embodiments of the invention, when the biomacromolecules are alginic acid, the molecular chains of the alginic acids can be cross-linked to form a cross-linked network by adding calcium ions into the prepared scaffold material; when the biomacromolecules are hyaluronic acid and polyglutamic acid, the molecular chains of both the hyaluronic acid and polyglutamic acid can be cross-linked to form a cross-linked network by adding adipic dihydrazide into the prepared scaffold material; and when the biomacromolecules are chitosan and polylysine, the molecular chains of both the chitosan and polylysine can be cross-linked to form a cross-linked network by adding genipin into the prepared scaffold material. The formation of those cross-linked networks can improve the mechanical strength of the scaffold materials, and adjust the porosity.

Those ordinarily skilled in the art should understand that the descriptions of any one of the above embodiments are merely illustrative, and do not aim to imply that the scope (claims inclusive) of the present disclosure is limited by those embodiments. On the basis of the concept of the invention, the above embodiments or technical characteristics of different embodiments can be combined, and there are a lot of other modifications different from the invention, which are mentioned in detail for concise expression. Therefore, any modifications, equivalent changes and improvements made on the basis of the concept and principle of the invention shall fall within the protective scope of the invention.

What is claimed is:

1. A method of making a catechol group modified biomacromolecular scaffold material wherein dopamine is taken as a functional group to physically or chemically modify biomacromolecules with a compound containing the catechol group, wherein the biomacromolecules are selected from the group consisting of alginic acid, hyaluronic acid, polyglutamic acid, chitosan, polylysine, and combinations thereof.

2. The method according to claim 1 wherein the modifying comprises:
   1) subjecting the compound containing catechol groups and the biomacromolecules to amidation to obtain modified biomacromolecules;
   2) generating polydopamine particles by self-polymerization of dopamine in an aqueous solution of ammonia;
   3) forming a scaffold having three cross-linking structures of modified biomacromolecules, modified biomacromolecules/polydopamine, and biomacromolecules/polydopamine through interaction between the catechol groups, interaction between the catechol groups and the polydopamine particles, and interaction between the biomacromolecules and the polydopamine particles; and 3) further cross-linking the scaffold of step 2) with calcium ions to obtain a gradient scaffold material.

3. The method according to claim 1 wherein when the biomacromolecules are alginic acid, hyaluronic acid or polyglutamic acid, the compound containing the catechol group is dopamine; and when biomacromolecules are chitosan or polylysine, the compound containing the catechol group is 3,4-dihydroxyphenylpropionic acid.

4. The method according to claim 1 wherein the feeding ratio of the biomolecules to the compound containing the catechol group is within the range of 2:1-1:5, and the degree of substitution of the catechol group in the biomolecules is within the range of 16-60%.

5. The method according to claim 2 wherein during the preparation process of the polydopamine particles, the amount of ammonia water is within the range of 0.5-3.5 mL, and the particle size of the obtained polydopamine particles is within the range of 150-560 nm.

6. The method according to claim 2 wherein the concentration of the calcium ions is 5%.

7. The method according to claim 2 wherein the porosity of the gradient scaffold material is within the range of 88-91%.

8. A method of making a catechol group modified biomacromolecular scaffold material comprising:

I.
1) reacting biomacromolecules with a compound containing catechol groups to perform amidation and obtain catechol group modified biomacromolecules;
2)
   a) freeze-drying the catechol group modified biomacromolecules of step 1) to obtain a freeze-dried catechol group modified biomacromolecular material; or, in the alternative,
   b) mixing the catechol group modified biomacromolecules of step 1) with polydopamine to obtain a mixture of the catechol group modified biomacromolecules and polydopamine and then freeze-drying the mixture of the catechol group modified biomacromolecules and polydopamine to obtain a catechol group modified biomacromolecules/polydopamine compound material; and
3) cross-linking the freeze-dried catechol group modified biomacromolecular material of step 2.a) or the catechol group modified biomacromolecules/polydopamine compound material of step 2.b) with a cross-linking agent to obtain the catechol group modified biomacromolecular compound scaffold material.

9. The method according to claim 8 wherein the biomacromolecules are selected from the group consisting of alginic acid, hyaluronic acid, polyglutamic acid, chitosan, polylysine, and combinations thereof.

10. The method according to claim 9 wherein when the biomacromolecules are alginic acid, the cross-linking agent is calcium salt;

when the biomacromolecules are hyaluronic acid or polyglutamic acid, the cross-linking agent is adipic dihydrazide;

and when the biomacromolecules are chitosan or polylysine, the cross-linking agent is genipin.

11. The method according to claim 8 further comprising forming the polydopamine by oxidized polymerization of dopamine.

12. The method according to claim 8 wherein the compound containing the catechol groups is dopamine or 3,4-dihydroxyphenylpropionic acid.

13. The method according to claim 12 wherein when the biomacromolecules are alginic acid, hyaluronic acid or polyglutamic acid, the compound containing the catechol groups is dopamine;

and when the biomacromolecules are chitosan or polylysine, the compound containing the catechol groups is 3,4-dihydroxyphenylpropionic acid.

14. The method according to claim 8 wherein the feeding ratio of the biomolecules to the compound containing the catechol groups is within the range of 2:1-1:5.

15. The method according to claim 8 wherein the degree of substitution of the catechol groups in the biomolecules is within the range of 16-60%.

16. The method according to claim 8 wherein the porosity of the catechol group modified biomacromolecular scaffold material is within the range of 88-91%.

17. A method of making a catechol group modified biomacromolecular scaffold material comprising:

1) mixing biomacromolecules with polydopamine to obtain a mixture of the biomacromolecules with the polydopamine,
2) freeze-drying the mixture of the biomacromolecules and polydopamine of step 1) to obtain a freeze-dried biomacromolecules/polydopamine compound material; and
3) cross-linking the freeze-dried biomacromolecules/polydopamine compound material of 2) with a cross-linking agent to obtain the catechol group modified biomacromolecular scaffold material.

* * * * *